(12) United States Patent
Chai

(10) Patent No.: US 9,326,734 B1
(45) Date of Patent: May 3, 2016

(54) METHOD OF COMPRESSING ELECTROCARDIOGRAPHY SIGNAL AND ELECTROCARDIOGRAPHY SIGNAL SENSING APPARATUS THEREOF

(71) Applicant: Sunplus Technology Co., Ltd., Hsinchu (TW)

(72) Inventor: Yea-Yen Chai, Hsinchu (TW)

(73) Assignee: Sunplus Technology Co., Ltd., Hsinchu (TW)

( * ) Notice: Subject to any disclaimer, the term of this patent is extended or adjusted under 35 U.S.C. 154(b) by 0 days.

(21) Appl. No.: 14/613,365

(22) Filed: Feb. 4, 2015

(51) Int. Cl.
    *A61B 5/04*      (2006.01)
    *A61B 5/00*      (2006.01)
    *A61B 5/0402*      (2006.01)

(52) U.S. Cl.
    CPC .............. *A61B 5/7232* (2013.01); *A61B 5/0402* (2013.01)

(58) Field of Classification Search
    CPC .......................... A61B 5/7232; A61B 5/0402
    See application file for complete search history.

(56) References Cited

U.S. PATENT DOCUMENTS

| | | | |
|---|---|---|---|
| 5,657,398 A * | 8/1997 | Guilak | 382/232 |
| 2006/0059324 A1 * | 3/2006 | Simske et al. | 711/170 |

* cited by examiner

*Primary Examiner* — George Manuel
(74) *Attorney, Agent, or Firm* — Jianq Chyun IP Office

(57) ABSTRACT

A method of compressing an electrocardiography (ECG) signal and an ECG signal sensing apparatus thereof are provided. The method of compressing the ECG signal includes the following steps. A current first characteristic wave is identified and captured from the ECG signal. A set of difference is obtained by subtracting a previous first characteristic wave from the current first characteristic wave. A first encoding process is executed on the set of difference, so as to obtain a first bit stream. A compressed ECG data is generated, wherein the compressed ECG data at least comprises the first bit stream.

8 Claims, 3 Drawing Sheets

METHOD OF COMPRESSING ELECTROCARDIOGRAPHY SIGNAL AND ELECTROCARDIOGRAPHY SIGNAL SENSING APPARATUS THEREOF

BACKGROUND

1. Technical Field

The invention relates to a signal processing method and a signal sensing apparatus, and particularly relates to a method for compressing an electrocardiography signal and an electrocardiography signal sensing apparatus.

2. Related Art

Heart disease is one of common major diseases. In order to avoid sudden death caused by the heart disease, doctors generally use an electrocardiogram (ECG) to early diagnose whether a person has the heart disease. Conventionally, the ECG provides a reliable determination reference to the doctor by recording potential variations of cardiocytes, so as to facilitate the doctor to effectively determine whether a person has the heart disease.

In order to describe a complete and continuous ECG, detection has to be continuously performed to obtain ECG data, though the large amount of ECG data usually causes difficulty in storage or transmission. In the conventional technique, the ECG data is compressed to facilitate storage and transmission, though most of the compression techniques are performed in a lossy compression mode, by which although a compression ratio is improved, the ECG data may have a distortion. Therefore, to provide an effective compression method and a related ECG signal sensing apparatus is still one of the objectives of the efforts of those skilled in the art.

SUMMARY

The invention is directed to a method for compressing electrocardiography (ECG) signal and an ECG signal sensing apparatus, by which characteristic waves in an ECG signal are continuously captured, and a plurality of differences between tandem characteristic waves are recorded, and the differences are encoded to achieve a lossless compression. In this way, under a premise of non-distortion of the ECG signal, the ECG signal is effectively compressed.

An exemplary embodiment of the invention provides a method for compressing an ECG signal, which includes following steps. A current first characteristic wave is identified and captured from the ECG signal. A set of difference is obtained by subtracting a previous first characteristic wave from the current first characteristic wave. A first encoding process is executed on the set of difference to obtain a first bit stream. A compressed ECG data including the first bit stream is generated in response to the first bit stream.

An exemplary embodiment of the invention provides an ECG signal sensing apparatus including a sensor, a capturing unit, a first calculation unit, a first encoding unit and a package unit. The sensor senses an ECG signal. The capturing unit is coupled to the sensor, and identifies and captures a current first characteristic wave from the ECG signal. The first calculation unit is coupled to the capturing unit, and obtains a set of difference by subtracting a previous first characteristic wave from the current first characteristic wave. The first encoding unit is coupled to the first calculation unit, and executes a first encoding process on the set of difference to obtain a first bit stream. The package unit is coupled to the capturing unit and the first encoding unit, and generates a compressed ECG data including the first bit stream in response to the first bit stream.

According to the above description, in the method for compressing the ECG signal of the invention, a first characteristic wave of each ECG signal is captured, and the current first characteristic wave and the previous first characteristic wave that are adjacent to each other on a time axis are subtracted to obtain a set of difference. An encoding process is executed on the set of difference to obtain a first bit stream, and an ECG data including the first bit stream can be stored or transmitted to other electronic apparatus for analysis. When the ECG data is decompressed (decoded), a comparison method is adopted to deduce the current first characteristic wave from the set of difference based on the previous first characteristic wave. In this way, a compression effect is effectively improved under a premise of lossless compression.

In order to make the aforementioned and other features and advantages of the invention comprehensible, several exemplary embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DETAILED DESCRIPTION OF DISCLOSED EMBODIMENTS

Figure 1:
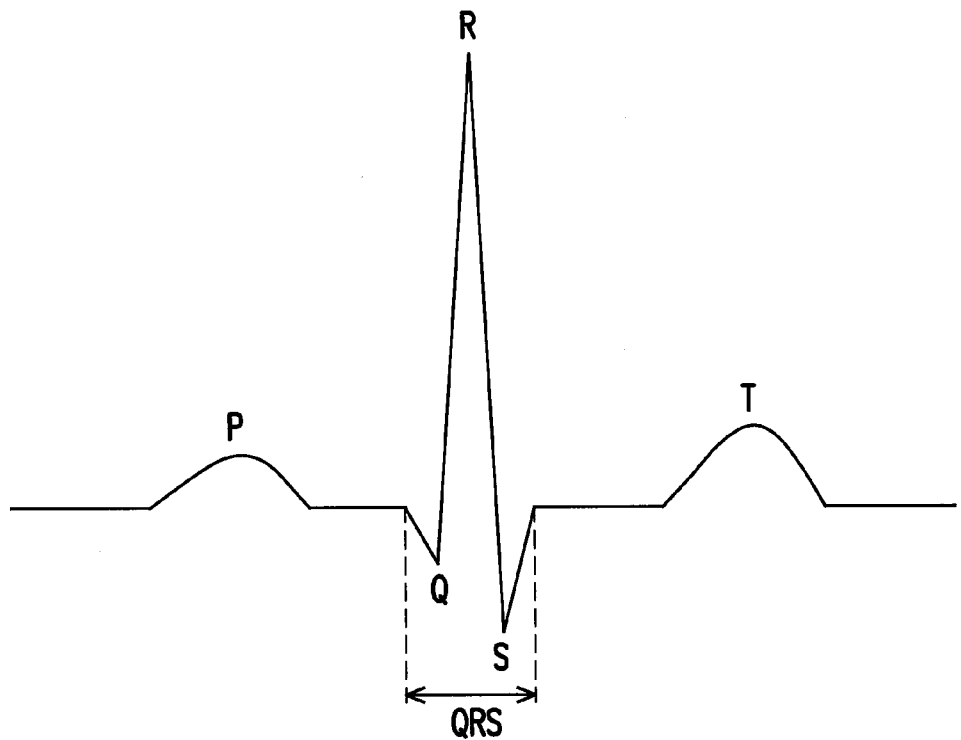
FIG. 1 is a schematic diagram of a characteristic wave in an electrocardiography (ECG) signal.

Reference will now be made in detail to the present preferred embodiments of the invention, examples of which are illustrated in the accompanying drawings. Wherever possible, the same reference numbers are used in the drawings and the description to refer to the same or like parts.

FIG. 1 is a schematic diagram of a characteristic wave in an electrocardiography (ECG) signal. Referring to FIG. 1, in an ECG signal, an ideal and complete characteristic wave corresponds to a potential variation status of cardiocytes in one cardiac action cycle. The characteristic wave includes a P-wave, a QRS-wave group (a wave group composed of a Q-wave, an R-wave and an S-wave), a T-wave, etc., which respectively correspond to an atrial depolarization phase, a ventricular depolarization phase and a ventricular repolarization phase. Besides, in view of a time axis, a time interval between two peaks of two adjacent R-waves is generally regarded as a time interval between two heart beats. In medicine, the aforementioned characteristic waves can be provided to medical staff or medical instrument for determination, comparison or analysis, so as to determine whether a provider of the ECG signal has a heart disease.

In order to achieve a better determination effect of the medical staff or the medical instrument, a feasible manner is to provide a large amount of the characteristic waves for comparison and analysis. In other words, a large amount of the ECG signals is required to be obtained. However, in order to avoid a situation that the obtained ECG signals occupy excessive storage space, the ECG signals are compressed to decrease the storage space required for storing the ECG signals, so as to improve an accessing efficiency.

Figure 2:
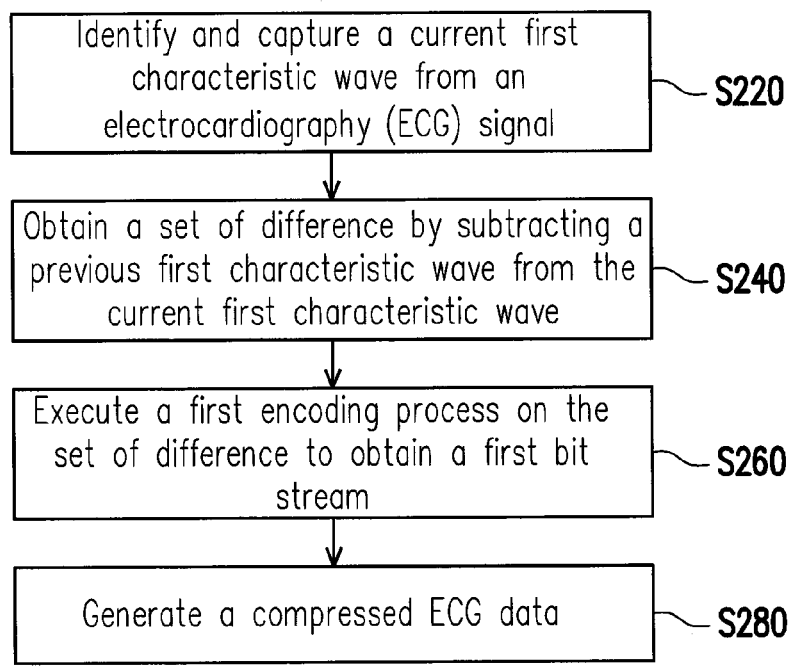
FIG. 2 is a flowchart illustrating a method for compressing an ECG signal according to an exemplary embodiment of the invention.

FIG. 2 is a flowchart illustrating a method for compressing an ECG signal according to an exemplary embodiment of the invention. Referring to FIG. 2, the present embodiment of the invention provides a method for compressing an ECG signal, which is adapted to an ECG signal sensing apparatus. First, a current first characteristic wave is identified and captured from the ECG signal (step S220). Then, a set of difference is obtained by subtracting a previous first characteristic wave from the current first characteristic wave (step S240). A first encoding process is executed on the set of difference to obtain a first bit stream (step S260). Finally, a compressed ECG data including the first bit stream is generated in response to the first bit stream (step S280).

Figure 3:
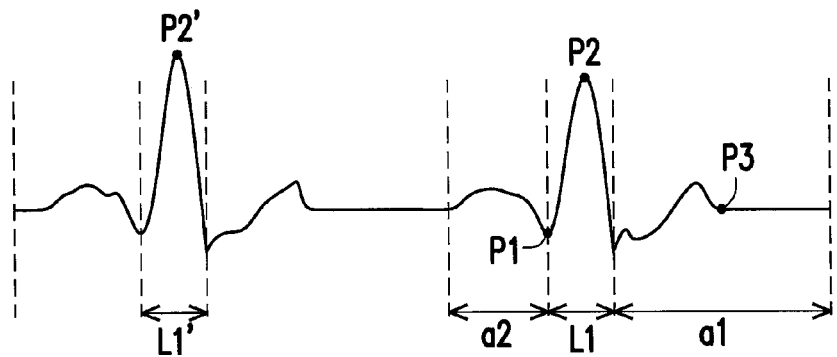
FIG. 3 is a schematic diagram of a first characteristic wave.

FIG. 3 is a schematic diagram of the first characteristic wave. Referring to FIG. 2 and FIG. 3, in order to avoid distortion, the method for compressing the ECG signal of the invention adopts lossless compression to improve the compression quality. Generally, Huffman coding is adopted to achieve the lossless compression. However, in view of inputting, the Huffman coding adopts ASCII characters and a range thereof is only 8 bits. Therefore, if a delta coding is performed to the ECG signal, at a part of the ECG signal with a larger variation rate, for example, a first characteristic wave L1 shown in FIG. 3 (a part of the QRS-wave group), a difference between a current and a previous signal values is probably quite large to exceed the aforementioned range. Now, a header code is required to be added to assist recording the difference generated under the delta coding. As a result, the efficiency of the Huffman coding is relatively low.

According to the above description, in the compression method of the present embodiment, after the ECG signal is received, the first characteristic wave L1 is first identified and captured from the ECG signal (step S220), so as to separate the first characteristic wave L1 from the ECG signal. In detail, after identifying the P-wave, the QRS-wave group, the T-wave, etc., the first characteristic wave L1 is correspondingly captured and recorded. An algorithm for identifying the QRS-wave group is, for example, a differential-based algorithm, a digital filter-based algorithm, an adaptive filter-based algorithm or a wavelet transform-based algorithm. It should be noticed that when the first characteristic wave L1 is identified and captured, related information of reference points on the ECG signal, for example, related information of a start point P1 of the first characteristic wave L1, a peak (R-wave peak) P2 of the first characteristic wave L1 and an offset point P3 of a second characteristic wave (the T-wave) are also obtained and recorded.

In the present embodiment, after the first characteristic wave L1 is obtained, a subtraction operation is performed to the first characteristic wave L1 and a previous first characteristic wave (for example, the first characteristic wave L1' of FIG. 3) to obtain the set of difference (the step S240). In other words, in the compression method of the invention, the subtraction operation is performed to the first characteristic wave L1 and the first characteristic wave L1' located adjacent to each other on the time axis to obtain the set of difference. When the subtraction operation is executed, the peak P2 of the first characteristic wave L1 and the peak P2' of the first characteristic wave L1' can be used to assist aligning the first characteristic waves L1 and L1'. Then, the first encoding process is executed on the set of difference to obtain the first bit stream (step S260), where the first coding process comprises the Huffman coding. Based on similarity of each of the ECG signals in waveform, it is expected that the difference obtained by subtracting the first characteristic wave L1' from the first characteristic wave L1 is avoided to be too large to influence the efficiency of the Huffman coding.

Finally, the compressed ECG data including the first bit stream is generated in response to the first bit stream (the step S280). In an embodiment of the invention, the compressed ECG data is, for example, a commonly used packet format in network transmission. It should be noticed that regarding a plurality of continuously obtained ECG signals, the aforementioned compression method is repeatedly executed to generate a plurality of compressed ECG data corresponding to a plurality of the first characteristic waves.

Figure 4:
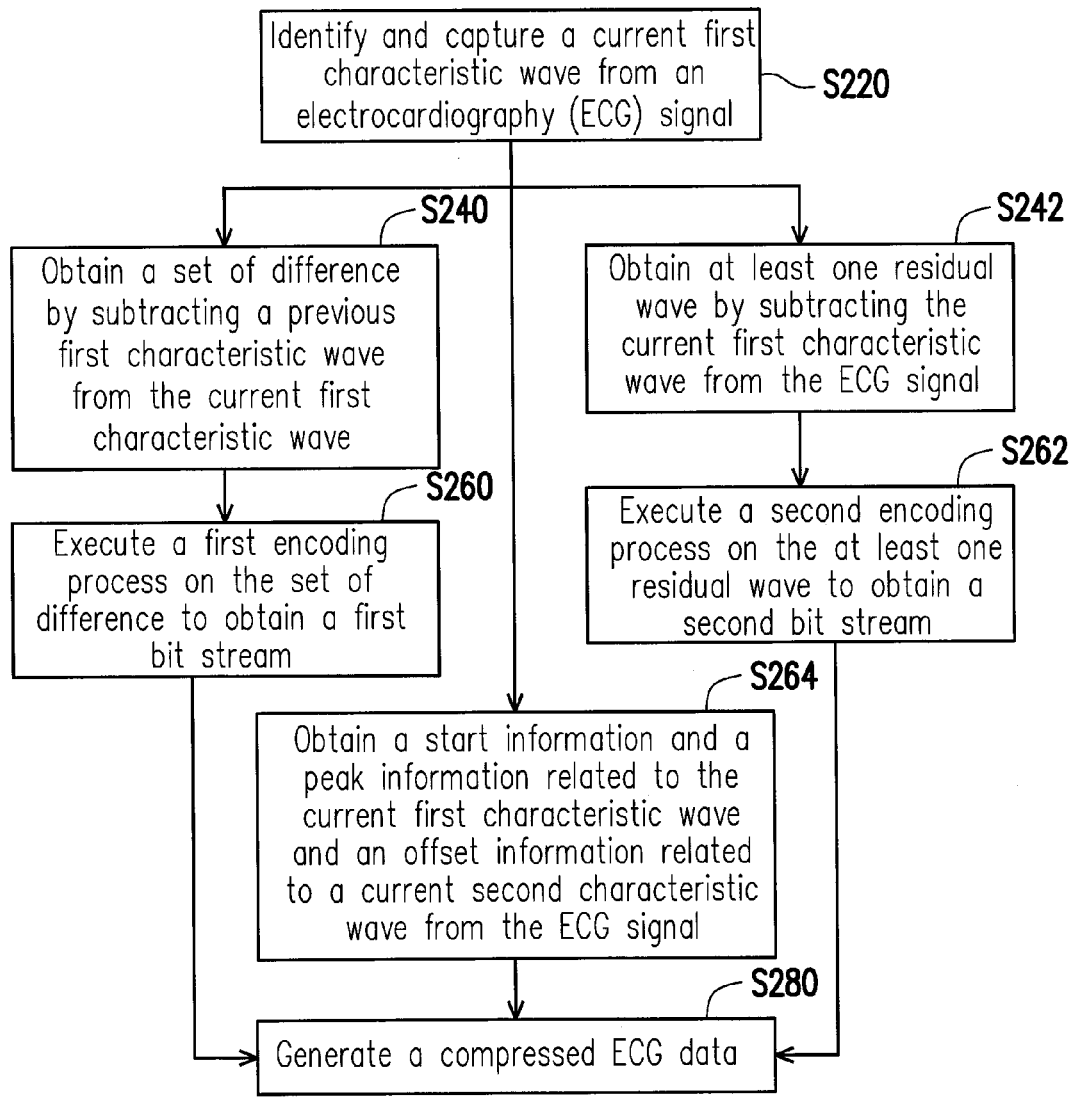
FIG. 4 is a flowchart illustrating a method for compressing an ECG signal according to another exemplary embodiment of the invention.

The aforementioned method for compressing the ECG signal is implemented based on the first characteristic wave L1 with a larger variation rate, though the invention is not limited thereto. FIG. 4 is a flowchart illustrating a method for compressing an ECG signal according to another exemplary embodiment of the invention. Referring to FIG. 3 and FIG. 4, in the present embodiment, after the current first characteristic wave (i.e. the first characteristic wave L1) is identified and captured (the step S220), the first characteristic wave L1 is further subtracted from the ECG signal to obtain at least one residual wave a1 and a2 (step S242). Obviously, compared to the first characteristic wave L1, a variation rate of the residual waves a1 and a2 is relatively low. Then, the second encoding process is executed on the residual waves a1 and a2 to obtain a second bit stream (step S262). The second encoding process includes a differential coding process and the Huffman coding process. Finally, a compressed ECG data including the first bit stream and the second bit stream is generated in response to the first bit stream and the second bit stream (the step S280). It should be noticed that, in the compressed ECG data, the first bit stream is generally added with an indicator header code, so as to distinguish with the second bit stream.

In the present embodiment, since the compressed ECG data includes the first bit stream and the second bit stream, it retains a more complete ECG signal. Moreover, as shown in FIG. 4, the method for compressing the ECG signal further includes obtaining a start information, a peak information related to the current first characteristic wave and an offset information related to a current second characteristic wave following the current first characteristic wave from the ECG signal (step S264). Referring to FIG. 3, the start information, the peak information and the offset information are respectively related information of the start point P1 of the first characteristic wave L1, the peak P2 of the first characteristic wave L1 and the offset point P3 of the second characteristic wave. The aforementioned related information is added to the compressed ECG data. When the compressed ECG data is decoded, the related information can be used to combine the first bit stream and the second bit stream to correctly implement the decoding to obtain the ECG signal.

As described above, the compressed ECG data is, for example, a commonly used packet format in network transmission, and is adapted to be transmitted from the ECG signal sensing apparatus to other electronic apparatuses, and is not limited by the invention. In another embodiment of the invention, the compressed ECG data can also be other data format suitable for storage. A method for decompressing (decoding) the compressed ECG data is opposite to the compression method shown in FIG. 2 or FIG. 4. To be specific, the first bit stream and the second bit stream are obtained from the compressed ECG data, and a Huffman decoding process is performed on the first bit stream to obtain a set of difference, and the current first characteristic wave is obtained according to the previous first characteristic wave and the set of difference. On the other hand, the Huffman decoding process and a differential decoding process are performed on the second bit stream to obtain at least one residual wave. The current first characteristic wave and the at least one residual wave are combined according to the start information and the peak information related to the current first characteristic wave and the offset information related to the current second characteristic wave, so as to restore a complete ECG signal.

Figure 5:
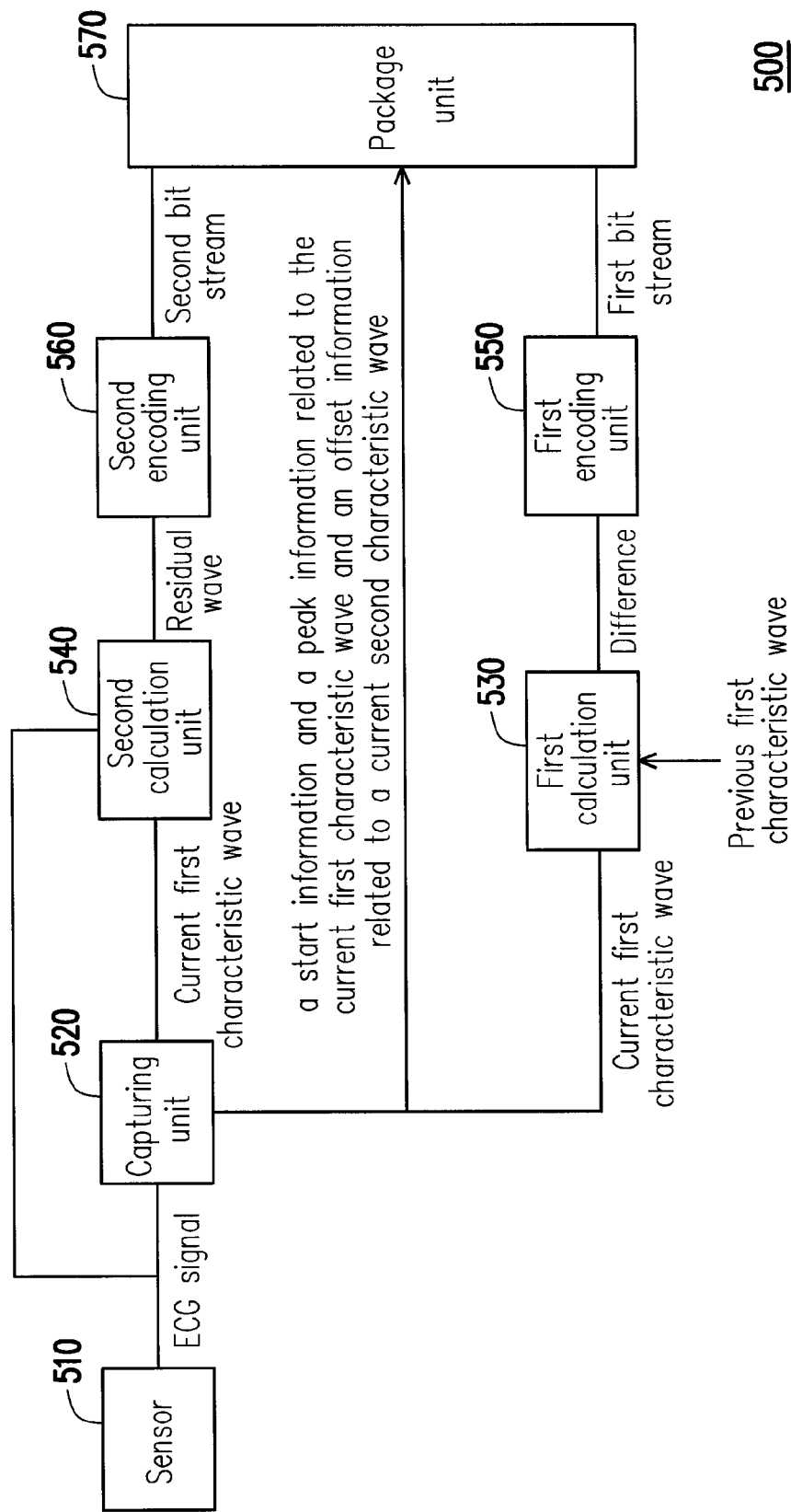
FIG. 5 is a schematic diagram of an ECG signal sensing apparatus according to an exemplary embodiment of the invention.

FIG. 5 is a schematic diagram of an ECG signal sensing apparatus according to an exemplary embodiment of the invention. Referring to FIG. 5, the ECG signal sensing apparatus 500 includes a sensor 510, a capturing unit 520, a first calculation unit 530, a second calculation unit 540, a first encoding unit 550, a second encoding unit 560 and a package unit 570. The sensor 510 senses an ECG signal, and the capturing unit 520 is coupled to the sensor 510, and identifies and captures a current first characteristic wave from the ECG signal. The first calculation unit 530 is coupled to the capturing unit 520 and the sensor 510, and obtains a set of difference by subtracting a previous first characteristic wave from the current first characteristic wave. In the present embodiment, the first calculation unit 530 is, for example, a subtractor. The first encoding unit 530 is coupled to the first calculation unit 530, and executes a first encoding process on the set of difference to obtain a first bit stream. The first encoding process includes the Huffman coding process. The package unit 570 is coupled to the capturing unit 520 and the first encoding unit 550, and generates a compressed ECG data including the first bit stream.

On the other hand, the second calculation unit 540 is coupled to the capturing unit 520, and subtracts the current first characteristic wave from the ECG signal to obtain at least one residual wave. In the present embodiment, the second calculation unit 540 is, for example, a subtractor. The second encoding unit 560 is coupled to the second calculation unit 540 and the package unit 570. The second encoding unit 560 executes a second encoding process on the at least one residual wave to obtain a second bit stream, and transmits the second bit stream to the package unit 570. The second encoding process includes a differential coding process and the Huffman coding process, and the package unit 570 further generates a compressed ECG data including the second bit stream.

In the present embodiment, the capturing unit 520 further obtains a start information, a peak information related to the current first characteristic wave and an offset information related to the current second characteristic wave from the ECG signal. It should be noticed that the current second characteristic wave is located behind the current first characteristic wave on a time axis of the ECG signal. In detail, the capturing unit 520 can store the captured current first characteristic wave and a plurality of the aforementioned information to a memory device (not shown), and extract the stored current first characteristic wave to serve as the previous first characteristic wave during a next compression flow. Besides, the capturing unit 520 also transmits the aforementioned information to the package unit 570. When the package unit 570 generates the compressed ECG data, the package unit 570 adds the start information, the peak information and the offset information to the compressed ECG data. In other words, the package unit 570 generates the compressed ECG data including the first bit stream, the second bit stream, the start information, the peak information and the offset information in response to the first bit stream, the second bit stream, the start information, the peak information and the offset information.

Detailed operation and setting of the ECG signal sensing apparatus 500 may refer to the aforementioned method for compressing the ECG signal, and details thereof are not repeated. The capturing unit 520, the first calculation unit 530, the second calculation unit 540, the first encoding unit 550, the second encoding unit 560 and the package unit 570 mentioned in the aforementioned exemplary embodiment are, for example, hardware devices composed of logic circuit components, and can respectively execute the aforementioned function. However, these circuits can also be implemented by software programs or firmware programs stored in a hard disk (not shown) or a memory (not shown) of the ECG signal sensing apparatus 500. For example, in an embodiment, the software programs or firmware programs implementing the aforementioned functions are loaded to a microprocessor (not shown) of the ECG signal sensing apparatus 500 to respectively execute the aforementioned method steps.

In summary, in the method for compressing the ECG signal of the invention, the first characteristic wave of each ECG signal is captured, and the current first characteristic wave and the previous first characteristic wave that are adjacent to each other on a time axis are subtracted to obtain the set of difference. The encoding process of lossless compression is executed on the set of difference to obtain the first bit stream. Moreover, the residual wave obtained by subtracting the current first characteristic wave from the ECG signal is also encoded to obtain the second bit stream. The compressed ECG data including the first bit stream and the second bit stream can be stored or transmitted to other electronic apparatus for decoding and analysis. In this way, the efficiency of the coding process is improved without distortion of the ECG signal.

It will be apparent to those skilled in the art that various modifications and variations can be made to the structure of the invention without departing from the scope or spirit of the invention. In view of the foregoing, it is intended that the invention cover modifications and variations of this invention provided they fall within the scope of the following claims and their equivalents.

What is claimed is:

1. A method for compressing an electrocardiography signal, adapted to an electrocardiography signal sensing apparatus, and the method for compressing the electrocardiography signal comprising:

identifying and capturing a current first characteristic wave from the electrocardiography signal;

obtaining a set of difference by subtracting a previous first characteristic wave from the current first characteristic wave;

executing a first encoding process on the set of difference to obtain a first bit stream;

generating a compressed electrocardiography data comprising the first bit stream in response to the first bit stream;

obtaining at least one residual wave by subtracting the current first characteristic wave from the electrocardiography signal;

executing a second encoding process on the at least one residual wave to obtain a second bit stream; and generating the compressed electrocardiography data comprising the first bit stream and the second bit stream in response to the first bit stream and the second bit stream.

2. The method for compressing the electrocardiography signal as claimed in claim 1, wherein the first encoding process comprises a Huffman coding process.

3. The method for compressing the electrocardiography signal as claimed in claim 1, wherein the second encoding process comprises a differential coding process and a Huffman coding process.

4. The method for compressing the electrocardiography signal as claimed in claim 1, further comprising:
   obtaining a start information and a peak information related to the current first characteristic wave and an offset information related to a current second characteristic wave following the current first characteristic wave from the electrocardiography signal; and
   generating the compressed electrocardiography data comprising the first bit stream, the second bit stream, the start information, the peak information and the offset information in response to the first bit stream, the second bit stream, the start information, the peak information and the offset information.

5. An electrocardiography signal sensing apparatus, comprising:
   a sensor, sensing an electrocardiography signal;
   a capturing unit, coupled to the sensor, and identifying and capturing a current first characteristic wave from the electrocardiography signal;
   a first calculation unit, coupled to the capturing unit and the sensor, and obtaining a set of difference by subtracting a previous first characteristic wave from the current first characteristic wave;
   a first encoding unit, coupled to the first calculation unit, and executing a first encoding process on the set of difference to obtain a first bit stream;
   a package unit, coupled to the capturing unit and the first encoding unit, and generating a compressed electrocardiography data comprising the first bit stream in response to the first bit stream;
   a second calculation unit, coupled to the capturing unit, and obtaining at least one residual wave by subtracting the current first characteristic wave from the electrocardiography signal; and
   a second encoding unit, coupled to the second calculation unit and the package unit, and executing a second encoding process on the at least one residual wave to obtain a second bit stream, wherein the package unit generates the compressed electrocardiography data comprising the first bit stream and the second bit stream in response to the first bit stream and the second bit stream.

6. The electrocardiography signal sensing apparatus as claimed in claim 5, wherein the first encoding process comprises a Huffman coding process.

7. The electrocardiography signal sensing apparatus as claimed in claim 5, wherein the second encoding process comprises a differential coding process and a Huffman coding process.

8. The electrocardiography signal sensing apparatus as claimed in claim 5, wherein the capturing unit obtains a start information and a peak information related to the current first characteristic wave and an offset information related to a current second characteristic wave following the current first characteristic wave from the electrocardiography signal, wherein the package unit generates the compressed electrocardiography data comprising the first bit stream, the second bit stream, the start information, the peak information and the offset information in response to the first bit stream, the second bit stream, the start information, the peak information and the offset information.

* * * * *